US012669415B2

(12) United States Patent
Oshita

(10) Patent No.: US 12,669,415 B2
(45) Date of Patent: Jun. 30, 2026

(54) ODOR MEASUREMENT DEVICE, CONTROL DEVICE, AND ODOR DETERMINATION METHOD

(71) Applicant: TAIYO YUDEN CO., LTD., Tokyo (JP)

(72) Inventor: Junji Oshita, Tokyo (JP)

(73) Assignee: TAIYO YUDEN CO., LTD., Tokyo (JP)

( * ) Notice: Subject to any disclaimer, the term of this patent is extended or adjusted under 35 U.S.C. 154(b) by 358 days.

(21) Appl. No.: 18/306,521

(22) Filed: Apr. 25, 2023

(65) Prior Publication Data

US 2023/0266206 A1     Aug. 24, 2023

Related U.S. Application Data

(63) Continuation of application No. PCT/JP2020/040987, filed on Oct. 30, 2020.

(51) Int. Cl.
*G01N 5/02* (2006.01)
*G01N 1/22* (2006.01)
(Continued)

(52) U.S. Cl.
CPC ......... *G01N 1/2214* (2013.01); *G01N 1/2205* (2013.01); *G01N 1/2273* (2013.01); *G01N 1/24* (2013.01); *G01N 33/0029* (2013.01)

(58) Field of Classification Search
CPC .. G01N 1/2214; G01N 1/2205; G01N 1/2273; G01N 1/24; G01N 33/0029;
(Continued)

(56) References Cited

U.S. PATENT DOCUMENTS 11,054,347 B1 * 7/2021 Gogoana .............. G01N 1/2214
2016/0084787 A1 * 3/2016 Ahn ........................ H05B 3/262
73/31.06
(Continued)

FOREIGN PATENT DOCUMENTS

JP        10-19862 A      1/1998
JP        2002022694 A  * 1/2002  .............. G01N 1/24
(Continued)

OTHER PUBLICATIONS

Japanese Office Action dated Nov. 26, 2024 in a counterpart Japanese patent application No. 2022-558788.
(Continued)

*Primary Examiner* — Robert R Raevis
(74) *Attorney, Agent, or Firm* — CHEN YOSHIMURA LLP

(57) ABSTRACT

An odor measurement device includes a sensor having an adsorption film that adsorbs an odorant and outputting a signal corresponding to adsorption of the odorant, a first pump that supplies a first gas containing an odorant to a housing chamber that houses the sensor, a second pump that supplies a second gas for desorbing the odorant from the adsorption film to the housing chamber, and a control device including a determination unit that measures the odorant based on information on an output signal of the sensor in a desorption process in which the odorant is desorbed from the adsorption film, and a control unit that sequentially executes a first mode in which the first gas is supplied to the housing chamber and a second mode in which the second gas is supplied to the housing chamber and the odorant is measured by the determination unit.

8 Claims, 9 Drawing Sheets

(51) Int. Cl.
    *G01N 1/24*         (2006.01)
    *G01N 33/00*      (2006.01)

(58) Field of Classification Search
    CPC ...... G01N 5/02; G01N 19/00; G01N 33/0031;
                         G01N 33/497; G01N 33/0032
    USPC .... 73/23.2, 23.31, 23.34, 24.01, 24.04–24.6,
                      73/25.01–25.5, 29.5, 31.01–31.3,
                      73/30.01–31.7, 863.21, 863.24
    See application file for complete search history.

(56)              References Cited

U.S. PATENT DOCUMENTS

| | | | |
|---|---|---|---|
| 2017/0199159 A1 | 7/2017 | Kuroki et al. | |
| 2021/0055275 A1* | 2/2021 | Park | F25D 17/042 |
| 2022/0236225 A1 | 7/2022 | Hattori et al. | |

FOREIGN PATENT DOCUMENTS

| | | | | |
|---|---|---|---|---|
| JP | 2006-064554 A | 3/2006 | | |
| JP | 2020-176989 A | 10/2020 | | |
| WO | 2007/010617 A1 | 1/2007 | | |
| WO | 2016/031080 A1 | 3/2016 | | |
| WO | WO-2020050110 A1 * | 3/2020 | ............ | B08B 7/005 |
| WO | WO 2020/202338 | * | 10/2020 | |

OTHER PUBLICATIONS

English translation of Written Opinion (PCT/ISA/237) issued in PCT/JP2020/040987 mailed in Jan. 2021.
International Search Report (ISR) issued in PCT/JP2020/040987 mailed in Jan. 2021.
Written Opinion (PCT/ISA/237) issued in PCT/JP2020/040987 mailed in Jan. 2021.

* cited by examiner

FIG. 6A
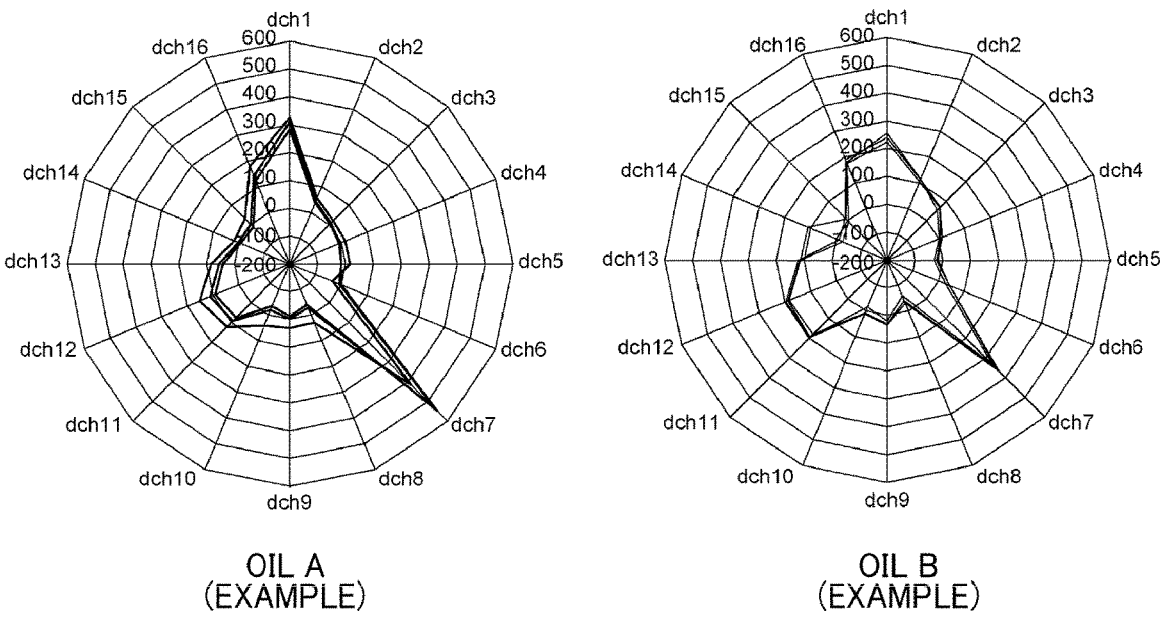
OIL A
(EXAMPLE)
FIG. 6B
OIL B
(EXAMPLE)
FIG. 6C
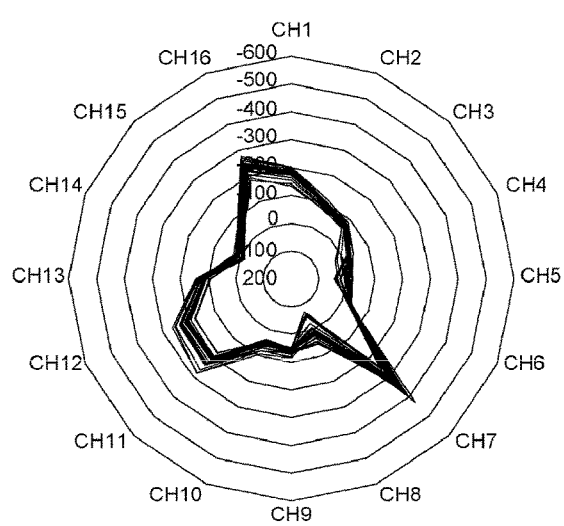
OIL A
(COMPARATIVE EXAMPLE)
FIG. 6D
OIL B
(COMPARATIVE EXAMPLE)

ODOR MEASUREMENT DEVICE, CONTROL DEVICE, AND ODOR DETERMINATION METHOD

FIELD

A certain aspect of the present disclosure relates to an odor measurement device, a control device, and an odor determination method.

BACKGROUND

In an odor measurement device using an odor sensor, an odor is measured by utilizing a change in electrical characteristics of the odor sensor caused by adhesion of an odorous substance contained in a gas to be measured to a sensing part of the odor sensor as disclosed in, for example, Japanese Patent Application Laid-Open No. 2006-64554 (Patent Document 1).

In the odor measurement device, after one odor sample is measured, a cleaning process of the sensing part is required. If the cleaning process is not performed, when the next odor sample is measured, the odorous substance adhering to the sensing part in the previous measurement causes a measurement error.

RELATED ART DOCUMENTS

Patent Documents

Japanese Patent Application Laid-Open No. 2006-64554

SUMMARY

In the above-mentioned cleaning process, it takes a long time to completely remove the odorous substance adhering to the sensing part, resulting in poor operating efficiency. Insufficient cleaning process also results in poor measurement accuracy.

Therefore, an object of the present disclosure is to provide an odor measurement device, a control device, and an odor determination method with high odor determination accuracy.

In one aspect of the present disclosure, there is provided an odor measurement device including: a sensor having an adsorption film that adsorbs an odorous substance and outputting a signal corresponding to adsorption of the odorous substance on the adsorption film; a housing chamber that houses the sensor; a first pump configured to supply a first gas containing an odorous substance to the housing chamber; a second pump configured to supply a second gas for desorbing the odorous substance from the adsorption film to the housing chamber; and a control device including: a determination unit configured to measure the odorous substance on the basis of information on an output signal of the sensor in a desorption process in which the odorous substance is desorbed from the adsorption film, and a control unit capable of sequentially executing a first mode in which the first gas is supplied to the housing chamber and a second mode in which the second gas is supplied to the housing chamber and the odorous substance is measured by the determination unit.

In the above configuration, the measurement for the odor determination is started from a state in which the odorous substance is adsorbed on the adsorption film, and the odor determination is performed based on the variation in the output signal of the sensor measured when the odorous substance is desorbed from the adsorption film. This allows the measurement to be performed while the adsorption state of the adsorption film at the start of measurement is always in a state in which the adsorption film is saturated with the odorous substance to be measured, and the accuracy of the odor determination is improved.

The control unit may execute the first mode for a period longer than that in the second mode. The determination unit may measure the odorous substance on the basis of the information on the output signal of the sensor in the desorption process in which the odorous substance adsorbed on the adsorption film in the first mode is desorbed from the adsorption film in the second mode.

The determination unit may measure the odorous substance by referring to information on variation in an output signal in the desorption process for each different odorous substance measured in advance by the sensor.

The information on variation in the output signal in the desorption process may be measured in advance for each different humidity condition, and the determination unit may measure the odorous substance by using information on humidity of the first gas acquired by a humidity sensor and referring to the information on variation in the output signal in the desorption process.

The odor measurement device may further include a filter that adsorbs an odorous substance contained in the first gas, and the second pump supplies the first gas that has passed through the filter to the housing chamber as the second gas.

The filter may include at least one of activated carbon, silica gel, zeolite, or allophane.

By using the filter in this manner, the entire device used for odor determination can be miniaturized.

The sensor may be provided in a plurality, and the plurality of odor sensors have different detection sensitivities depending on respective odorous substances.

This makes it possible to determine a plurality of types of odorous substances and to determine the odor with higher accuracy.

In another aspect of the present disclosure, there is provided a control device that measures an odorous substance based on information on an output signal of a sensor having an adsorption film that adsorbs the odorous substance, the control device including: a determination unit configured to measure the odorous substance on the basis of the information on the output signal of the sensor in a desorption process in which the odorous substance is desorbed from the adsorption film; and a control unit capable of sequentially executing a first mode in which a first gas containing the odorous substance is supplied to a housing chamber that houses the sensor and a second mode in which a second gas for desorbing the odorous substance from the adsorption film is supplied to the housing chamber.

In another aspect of the present disclosure, there is provided an odor determination method including: executing a first mode in which a first gas containing an odorous substance is supplied to a sensor, the sensor having an adsorption film that adsorbs the odorous substance and outputting a signal corresponding to adsorption of the odorous substance; executing, after the first mode, a second mode in which a second gas for desorbing the odorous substance from the adsorption film is supplied to the sensor to desorb the odorous substance adsorbed on the adsorption film; and measuring, in the second mode, the odorous substance based on the information on the output signal of the sensor in a desorption process in which the odorous substance is desorbed from the adsorption film.

BRIEF DESCRIPTION OF THE DRAWINGS

FIG. 6A to FIG. 6D are diagrams for comparing shapes of radar charts obtained when two types of oils different from each other are measured using the odor determination method of the embodiment and the conventional odor determination method;

DETAILED DESCRIPTION

Hereinafter, an embodiment of the present disclosure will be described with reference to the accompanying drawings.

In the present embodiment, an odor determination system including a plurality of odor sensors having adsorption films with different adsorption characteristics will be described.

In the following description, an odor refers to an aggregate of a plurality of types of odorous substances. That is, the odorous substances correspond to constituent components (odor components) of an odor. Since the adsorption film of each odor sensor has selectivity of the odorous substance to be adsorbed, different kinds of odorous substances are adsorbed onto the adsorption films of the odor sensors, respectively. In the present embodiment, the amount of each odorous substance measured by each odor sensor is comprehensively determined to determine the type of the odor, which is an aggregate of the odorous substances.

The details thereof will be described below.

[Configuration of Odor Determination System]

Figure 1:
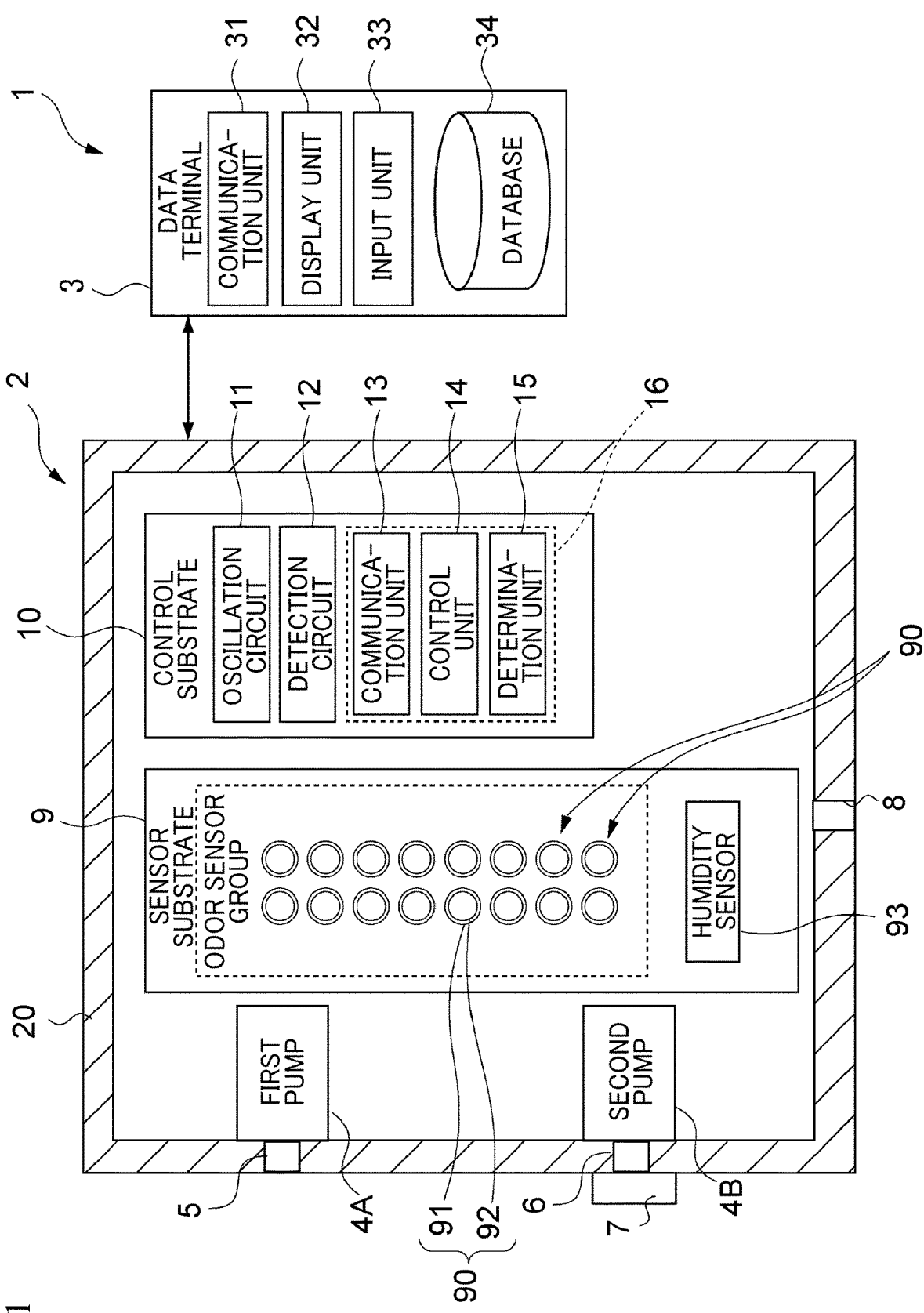
FIG. 1 is a schematic diagram illustrating a configuration of an odor determination system in accordance with an embodiment and configurations of an odor measurement device and a data terminal included in the odor determination system.

FIG. 1 is a schematic diagram illustrating a configuration of an odor determination system 1 in accordance with an embodiment, and configurations of an odor measurement device 2 and a data terminal 3 included in the odor determination system 1.

As illustrated in FIG. 1, the odor determination system 1 includes the odor measurement device 2 and the data terminal 3.

Configuration of Odor Measurement Device

The odor measurement device 2 includes a housing chamber 20, a first pump 4A, a second pump 4B, a first supply port 5, a second supply port 6, a filter 7, a discharge port 8, a sensor substrate 9, and a control substrate 10.

The sensor substrate 9 and the control substrate 10 are housed in the housing chamber 20 while being stacked, for example.

The housing chamber 20 is a processing chamber in which a series of processes related to odor determination is performed.

The first pump 4A is provided in the housing chamber 20. The operation of the first pump 4A supplies a first gas containing the odor to be determined into the housing chamber 20 through the first supply port 5. The first gas is, for example, a gas in an environment in which the odor measurement device 2 is installed, and is a gas around the odor measurement device 2, that is, outside air. The first gas is indicated by reference numeral 50 in FIG. 2.

The second pump 4B is installed in the housing chamber 20. The operation of the second pump 4B supplies a second gas into the housing chamber 20 through the second supply port 6. The second gas is a gas that desorbs the odorous substance adsorbed on the adsorption film of the odor sensor described later from the adsorption film. The second gas is a gas obtained after the first gas has passed through the filter 7 in the housing chamber 20. The second gas is indicted by reference numeral 51 in FIG. 2. As the first gas passes through the filter 7, the odor (or each odorous substance constituting the odor), moisture, and the like contained in the first gas are removed. That is, the second gas 51 is a gas different from the first gas 50.

Activated carbon, silica gel, zeolite, allophane or the like can be used for the filter 7. Typically, an activated carbon filter is used.

The second gas may be supplied into the housing chamber 20 without using the filter. For example, an inert gas or ozone is supplied as the second gas. In this case, an inert gas or an ozone generator is prepared. To miniaturize the odor measurement device 2, use of a filter is more preferable.

The gas in the housing chamber 20 can be discharged to the outside of the housing chamber 20 through the discharge port 8.

The sensor substrate 9 includes a plurality of odor sensors 90 and a humidity sensor 93 mounted on a wiring substrate. The number of the odor sensors 90 may be one or more, and an example in which 16 odor sensors 90 are provided is given in the present embodiment. The wiring substrate is a substrate having a wiring layer.

The odor sensor 90 detects gas. The odor sensor 90 is, for example, a quartz crystal microbalance (QCM) sensor. The odor sensor 90 includes a crystal oscillator 91, electrodes (not illustrated), and an adsorption film 92.

As the crystal oscillator 91, for example, an oscillator cut at a cut angle called AT-cut can be used. The crystal oscillator 91 has a thin plate shape. Electrodes obtained by patterning a metal thin film into a predetermined shape are formed on one main surface of the crystal oscillator 91 and the other main surface opposite to the main surface, respectively. The adsorption film 92 is formed on the electrode and adsorbs an odorous substance.

The adsorption films 92, which adsorb respective odorous substances, of the odor sensors 90 are composed of different materials. As described above, the odor contained in the gas to be determined contains one or more odorous substances (odor components). The odorous substance that each adsorption film 92 mainly adsorbs differs from the others. Since a plurality of (16 in the present embodiment) odor sensors 90 are provided and the odor sensors 90 have different adsorption films 92, a plurality of types of odorous substances can be detected. The odor sensors 90 have different detection sensitivities depending on odorous substances. The material used for the adsorption film is appropriately selected according to the type of the odorous substance to be measured. Hereinafter, examples of materials used for the adsorption film 92 of each odor sensor 90 will be described, but the combination of the materials is determined according to the type of the odor to be determined.

As the adsorption film, cellulose, a fluorine-based polymer, lecithin, a phthalocyanine compound, a porphyrin compound, polyimide, polypyrrole, polystyrene, an acrylic polymer, sphingomyelin, polybutadiene, polyisoprene, a polyvinyl alcohol-based polymer, UiO-66, MIL-125 (MOF), ZIF-8, or the like can be used.

The humidity sensor 93 detects the humidity of a gas such as the first gas or the second gas supplied into the housing chamber 20 and supplied to the adsorption film 92 of the odor sensor 90. A known humidity sensor can be used as the humidity sensor 93. The humidity sensor detects a relative humidity. Hereinafter, humidity refers to relative humidity. The information on humidity detected by the humidity sensor 93 is output to a determination unit 15 described later.

The control substrate 10 is provided with a power supply circuit, a signal processing circuit, and the like. The control substrate 10 is electrically connected to the sensor substrate 9, and the power supply circuit supplies necessary power to each odor sensor 90 and the humidity sensor 93 via a wiring layer on the sensor substrate. The signal processing circuit oscillates each odor sensor 90 and determines the type, strength, and the like of the odor (thereby measures the odor) to be determined based on the respective output signals of the odor sensors 90 and the humidity sensor 93. The signal processing circuit also controls the driving of the first pump 4A and the second pump 4B. In FIG. 1, the configuration of the control substrate 10 is mainly illustrated by a functional block diagram.

The control substrate 10 includes an oscillation circuit 11, a detection circuit 12, a communication unit 13, a control unit 14, and the determination unit 15. The communication unit 13, the control unit 14, and the determination unit 15 constitute a control device 16. The control device 16 controls a series of processes related to the determination of the type of the odor and the like.

The oscillation circuit 11 oscillates the crystal oscillator of each odor sensor 90 at a predetermined frequency. For example, the resonant frequency is 9 MHz.

The detection circuit 12 detects the resonant frequency of each odor sensor 90. When the odorous substance is adsorbed onto the adsorption film 92 of each odor sensor 90 while the odor sensor 90 is oscillated at a predetermined frequency by the oscillation circuit 11, the resonant frequency of the crystal oscillator of each odor sensor 90 varies. Further, when the odorous substance adsorbed on the adsorption film 92 of each odor sensor 90 is desorbed while the odor sensor 90 is oscillated at a predetermined frequency by the oscillation circuit 11, the amount of the odorous substance adsorbed on the adsorption film 92 decreases and the resonant frequency of the crystal oscillator of each odor sensor 90 varies. The resonant frequency detected by each odor sensor 90 is output from the detection circuit 12 to the determination unit 15. Hereinafter, the resonant frequency detected by each odor sensor 90 may be referred to as an output signal.

The communication unit 13 transmits and receives various kinds of information to and from an external device different from the odor measurement device 2, for example, the data terminal 3 or the like in a wireless or wired manner.

The determination unit 15 calculates the amount of variation in resonant frequency at the time of desorption of the odorous substance in each odor sensor 90 based on the electric signal of each odor sensor 90 input from the detection circuit 12 and measures the amount of each odorous substance from the calculation results. The determination unit 15 determines the type and strength of the odor to be determined based on the amount of each odorous substance measured by each odor sensor 90. More specifically, the determination unit 15 refers to information stored in a database 34, which will be described later, and determines/measures the type and strength of the odor. The determination results such as the amount of variation in resonant frequency of each odor sensor 90 calculated by the determination unit 15, the measured amount of each odorous substance, and the type of the odor determined based on the amount of each odorous substance are output to the data terminal 3 described later through the communication unit 13.

The control unit 14 controls the operation of the first pump 4A and the second pump 4B, controls the oscillation circuit 11 and the detection circuit 12, and controls the determination unit 15 in accordance with switching of modes described later.

Figures 2A, 2B:
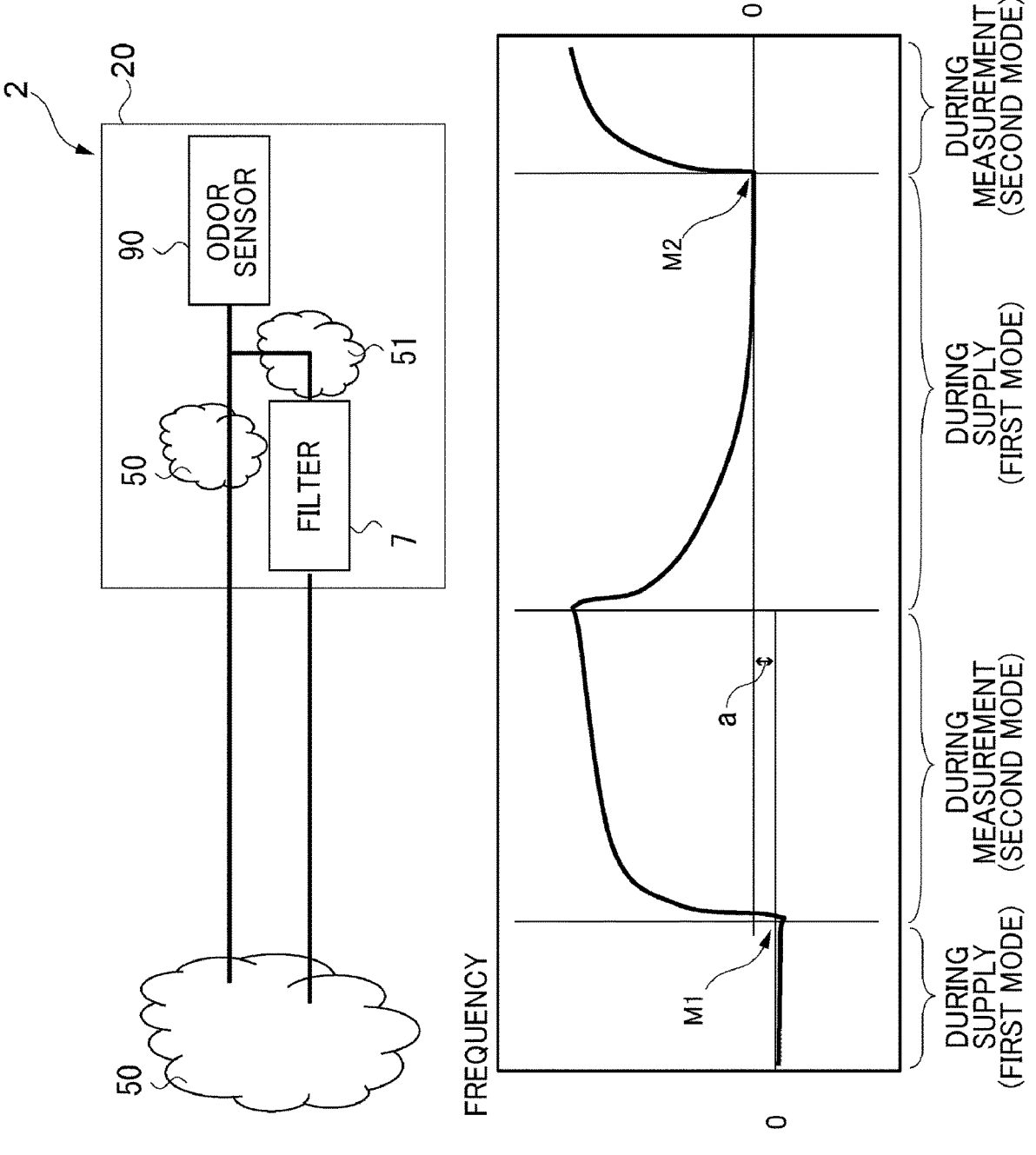
FIG. 2A and FIG. 2B are schematic diagrams for describing odor determination in accordance with the embodiment.

FIG. 2A is a schematic diagram for describing an odor determination method in the odor determination system in accordance with the present embodiment. FIG. 2B illustrates a temporal variation in resonant frequency measured by the odor sensor 90 in a series of processes related to the odor determination.

As illustrated in FIG. 2A and FIG. 2B, a series of processes according to the odor determination method of the present embodiment includes a step of supplying a gas containing an odor to be determined, which is a first mode, a measurement step, which is a second mode. Hereinafter, the step of supplying the gas containing the odor to be determined may be referred to as a supply step. In FIG. 2B, the period of the supply step is indicated as "during supply", and the period of the measurement step is indicated as "during measurement".

The supply step is a step of supplying the first gas 50 containing the odor to be determined to the adsorption film 92 of each odor sensor 90 to cause each adsorption film 92 to adsorb the odorous substance corresponding to the type of the adsorption film. In the supply step, the odor sensor 90 is adapted to the environment. Here, "adapted to the environment" means that the adsorption film 92 is exposed to the first gas 50 until adsorption and desorption of the odorous substance with respect to each adsorption film 92 are substantially in an equilibrium state by supplying the first gas 50 to the adsorption film 92 of the odor sensor 90.

In a series of processes related to the odor determination, the measuring step is performed after the supply step. In the measurement step, the second gas 51 is supplied to the adsorption film 92 to desorb the odorous substance adsorbed on the adsorption film 92, the resonant frequency, which is an output signal in the desorption process, is measured, and the amount of the odorous substance is measured based on the amount of variation in resonant frequency, which is the amount of variation in the output signal.

The control unit 14 switches between the first mode in which the inside of the housing chamber 20 is set to the processing environment of the supply process and the second mode in which the inside of the housing chamber 20 is set to the processing environment of the measurement process.

In the first mode, which is the supply step, the control unit 14 operates the first pump 4A. Thus, as illustrated in FIG. 2A, the first gas 50 is supplied into the housing chamber 20 through the first pump 4A. When the first gas 50 is supplied, each odor sensor 90 in the housing chamber 20 is exposed to the first gas 50, and odorous substances are adsorbed onto the respective adsorption films 92 of the odor sensors 90. In the supply step, the resonant frequency decreases in proportion to an increase in the mass of the odorous substance adsorbed on the adsorption film 92. The control unit 14 may control the oscillation circuit 11 and the detection circuit 12 so that they operate, during the supply step.

In the second mode, which is the measurement step, the control unit 14 operates the second pump 4B. Thus, as illustrated in FIG. 2A, the second gas 51 is supplied into the housing chamber 20 through the second pump 4B. When the second gas 51 is supplied, each odor sensor 90 in the housing chamber 20 is exposed to the second gas 51, and the odorous substances adsorbed on the respective adsorption films 92 of the odor sensors 90 are desorbed. In the measurement step, the odorous substance is desorbed from the adsorption film 92. Thus, the amount of the odorous substance adsorbed on the adsorption film 92 decreases, and the resonant frequency increases in proportion to the decrease in the mass of the odorous substance adsorbed on the adsorption film 92.

During the measurement step, the control unit 14 controls the oscillation circuit 11 and the detection circuit 12 so that they operate.

The control unit 14 acquires reference information used at the time of odor determination from the database 34 described later through the communication unit 13 and performs control such that the acquired information is output to the determination unit 15.

The control unit 14 performs control such that the information on the respective output signals of the odor sensors 90 acquired by the detection circuit 12 is output to the determination unit 15. The information on the output signals of the odor sensors 90 is information on the resonant frequencies associated with desorption of the respective odorous substances from the adsorption films 92. Further, the control unit 14 performs control such that the information on humidity detected by the humidity sensor 93 is output to the determination unit 15.

Further, the control unit 14 controls the determination unit 15 to measure the amount of the odorous substance based on the information stored in the database 34, the detection information of the odor sensors 90 acquired by the detection circuit 12, and the information on humidity detected by the humidity sensor 93.

Data Terminal

As illustrated in FIG. 1, the data terminal 3 includes a communication unit 31, a display unit 32, an input unit 33, and the database 34.

The communication unit 31 transmits and receives various kinds of information to and from the odor measurement device 2 and other external devices in a wireless or wired manner. The display unit 32 displays various kinds of information.

The display unit 32 is a known display device. For example, the variation in resonant frequency acquired from the odor measurement device 2 via the communication unit 31, the measurement result of the amount of the identified odorous substance, and the like are displayed on the display unit 32. The user can visually recognize information displayed on the display unit 32.

The input unit 33 is a keyboard, a touch panel, or the like, for example. The time for supplying the gas to be measured, the measurement time, and the like may be input and set by the user via the input unit 33.

The database 34 serving as a storage unit may store information on variation in the output signal in the desorption process for each odorous substance measured in advance by each odor sensor 90 of the odor measurement device 2.

The information is information on a variation in the output signal obtained when the odor sensor 90 is exposed to the first gas to cause the odorous substance to be adsorbed onto the adsorption film 92 and then the second gas is supplied to the odor sensor 90 to desorb the odorous substance adsorbed on the adsorption film 92. Hereinafter, the information on variation in the output signal when the odorous substance is desorbed may be referred to as information related to desorption. The information related to desorption may be measured in advance by each of the odor sensors 90 for each different humidity condition and each different odorous substance. For each different humidity condition and each different odorous substance, the information on the type of the odorous substance and the information on variation in the output signal in the desorption process acquired by each of the odor sensors 90 are stored in the database 34 in association with each other. The humidity is the humidity of the first gas and is measured by the humidity sensor 93.

In addition, the database 34 stores information on the quantitative ratio of odorous substances necessary for determining the odor. FIG. 6A and FIG. 6B are radar charts presenting the proportional relationship among the amounts of variations in resonant frequencies detected by respective odor sensors when measurement is performed using gases emitted from oil A and oil B having mutually different quantitative ratios of odorous substances using the odor determination method of the present embodiment described later. The radar chart is created with reference to the maximum value of the amount of the variation in resonant frequency calculated based on the resonant frequency detected by each odor sensor 90. As illustrated in FIG. 6A and FIG. 6B, different quantitative ratios of odorous substances produce different odor patterns. This can be used to determine the type of the odor.

Furthermore, the database 34 may store the information on variation in the output signal of each odor sensor 90 due to desorption of moisture, which is measured in advance for each different humidity condition. Hereinafter, the information on variation in the output signal due to the desorption of moisture may be referred to as information related to humidity. The information is information on variation in the output signal when the odor sensor 90 is exposed to a moisture-containing gas that does not contain an odorous substance to cause the moisture to be adsorbed onto the adsorption film 92, and then the moisture-containing gas that does not contain the odorous substance and has passed through the filter 7 is supplied to the odor sensor 90 to desorb the moisture adsorbed on the adsorption film 92. The humidity in this case is the humidity of the moisture-containing gas that does not pass through the filter 7 and contains no odorous substance. The humidity of the odor-free, moisture-containing gas is measured by the humidity sensor 93. The information on humidity measured by the humidity sensor 93 and the information on variation in the output signal due to the desorption of moisture acquired by each of the odor sensors 90 are stored in the database 34 in association with each other.

Depending on the type of the adsorption film 92, the adsorption film 92 may adsorb other substances (including an odorous substance and an odorless substance), moisture, and the like in addition to the odorous substance. The tendency of moisture adsorption also varies depending on the type of the adsorption film 92. In addition, the adsorption amount of moisture varies depending on the humidity of the gas.

The variation in resonant frequency measured when the odorous substance is desorbed from the adsorption film 92 on which the odorous substance has been adsorbed includes a variation due to desorption of the odorous substance adsorbed on the adsorption film 92 and a variation due to desorption of moisture. In the present embodiment, it is possible to calculate the amount of variation in resonant frequency due to the odorous substance by removing the amount of variation in resonant frequency due to moisture from the amount of variation in resonant frequency actually detected by the odor sensor 90 at the time of odor determination using the above-described information relating to humidity.

The configuration of the database 34 is not particularly limited, and is typically composed of a nonvolatile storage device such as a semiconductor memory or a hard disk drive (HDD). The database 34 is not limited to being installed indoors, and may be installed in another place via a wired or wireless network. Further, the database 34 may be composed of a cloud server or the like.

The database 34 is constructed by, for example, machine learning.

[Odor Determination Method]

Hereinafter, an embodiment of an odor determination method by the odor determination system 1 will be described in comparison with a conventional example.

FIG. 2A, FIG. 2B, FIG. 3, FIG. 4A, and FIG. 4B are diagrams related to the odor determination method of the present embodiment.

FIG. 7A, FIG. 7B, FIG. 8, FIG. 9A, and FIG. 9B are diagrams related to an odor determination method in a conventional example.

Figures 7A, 7B:
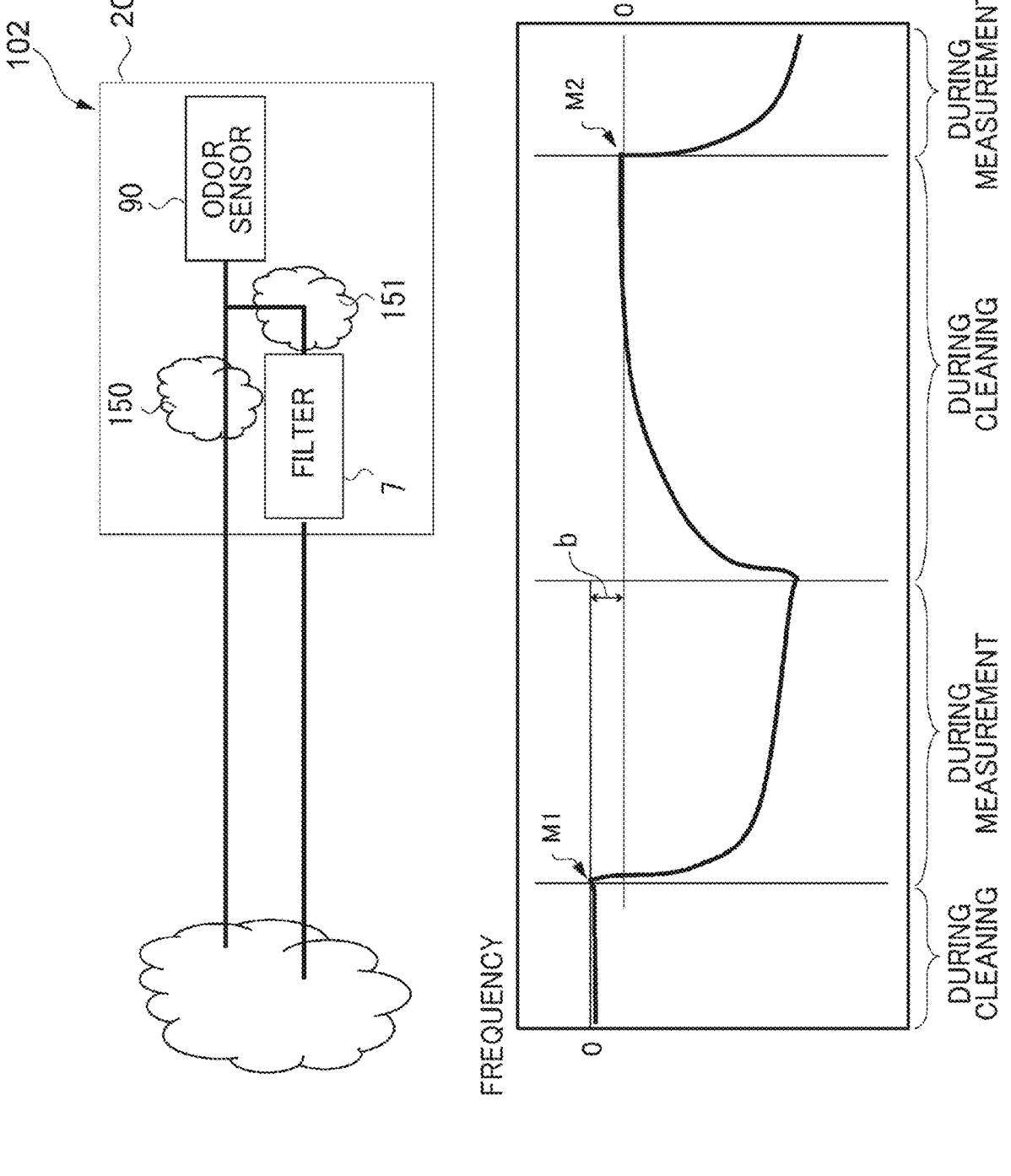
FIG. 7A and FIG. 7B are schematic diagrams for describing the conventional odor determination.

FIGS. 2A and 2B correspond to FIGS. 7A and 7B, respectively. FIG. 7A is a schematic diagram for describing the odor determination method in the conventional example. FIG. 7B illustrates a temporal variation in resonant frequency measured by the odor sensor in a series of processes related to the odor determination.

Figure 3:
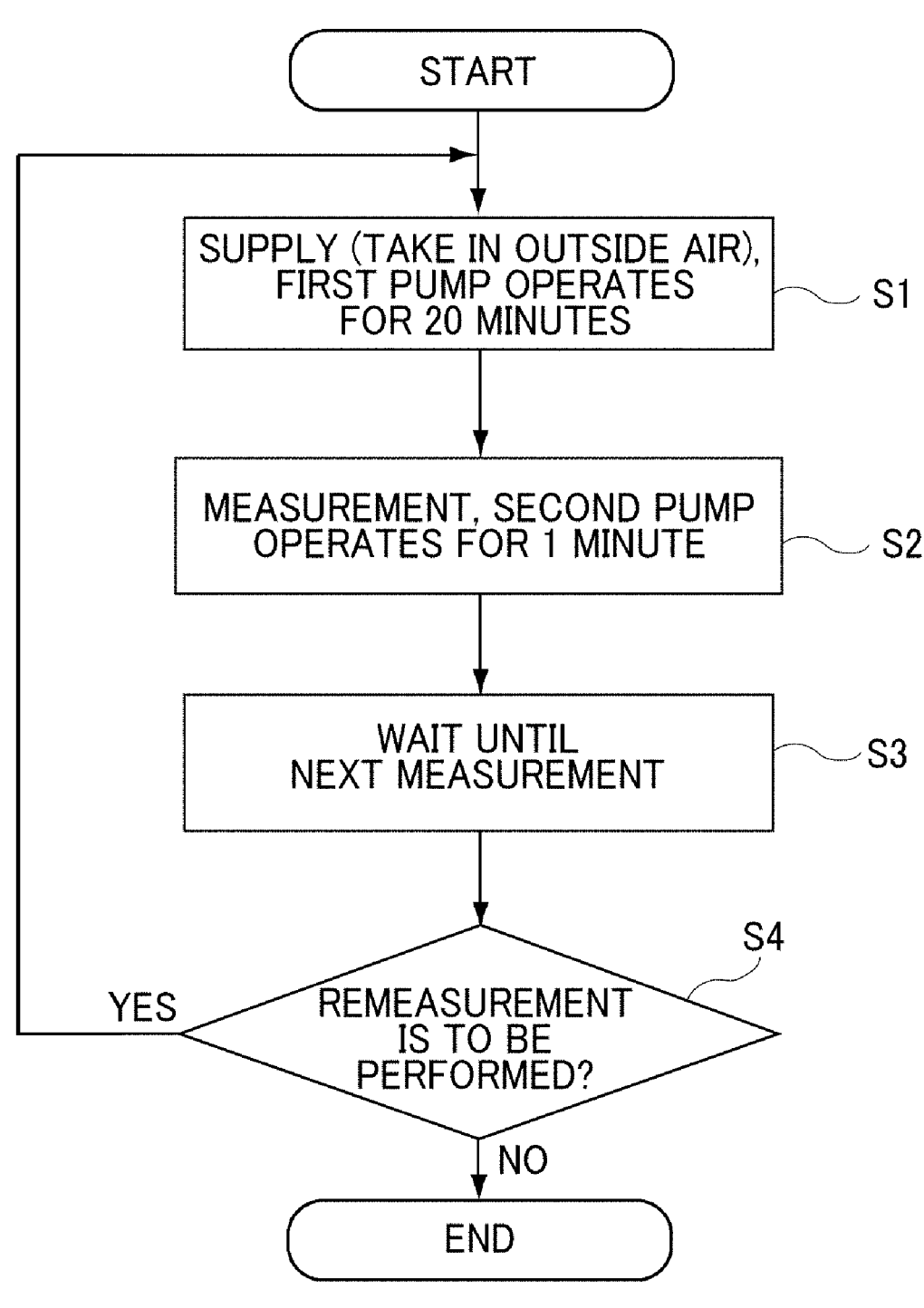
FIG. 3 is a flowchart of an odor determination method in accordance with the embodiment.
Figure 8:
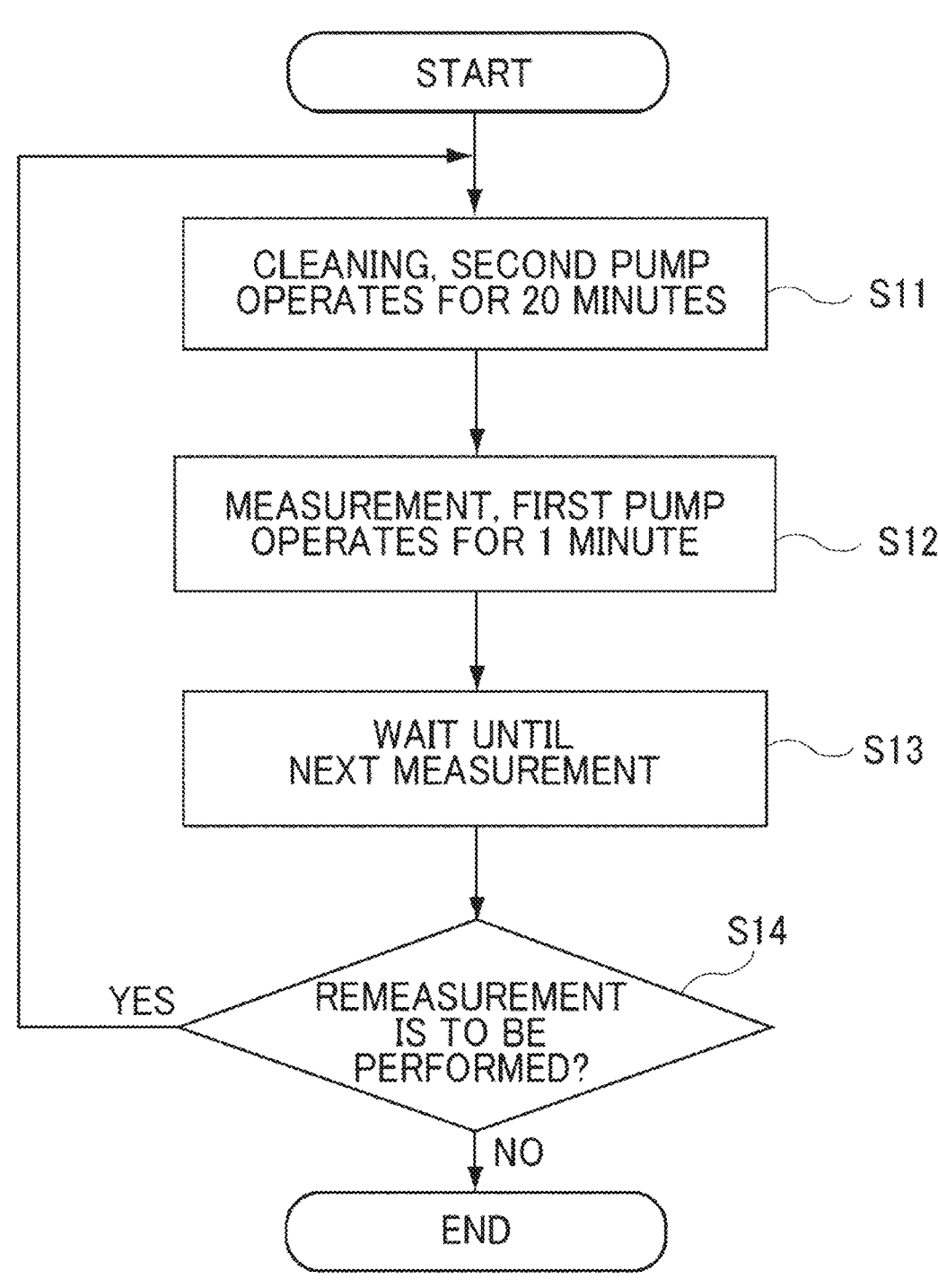
FIG. 8 is a flowchart of the conventional odor determination method.

FIG. 3 and FIG. 8 correspond to each other. FIG. 3 is a flowchart of the odor determination method of the present embodiment. FIG. 8 is a flowchart of the odor determination method in the conventional example.

Figure 4A:
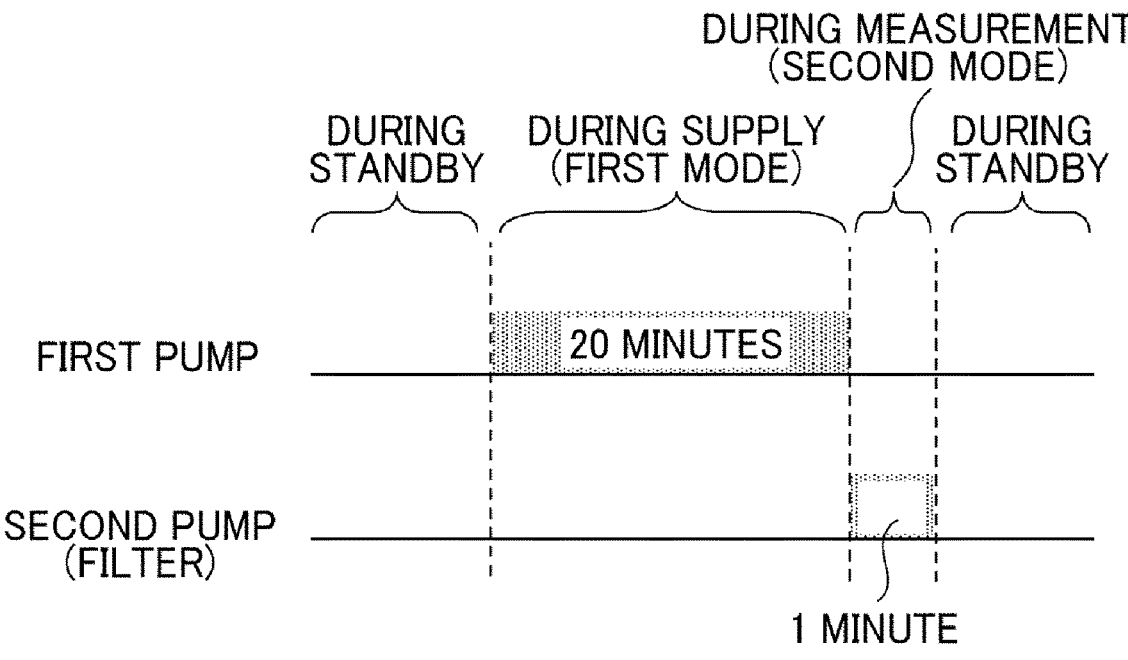
FIG. 4A is a diagram for describing operation states of pumps in the odor determination method in accordance with the embodiment.
Figure 4B:
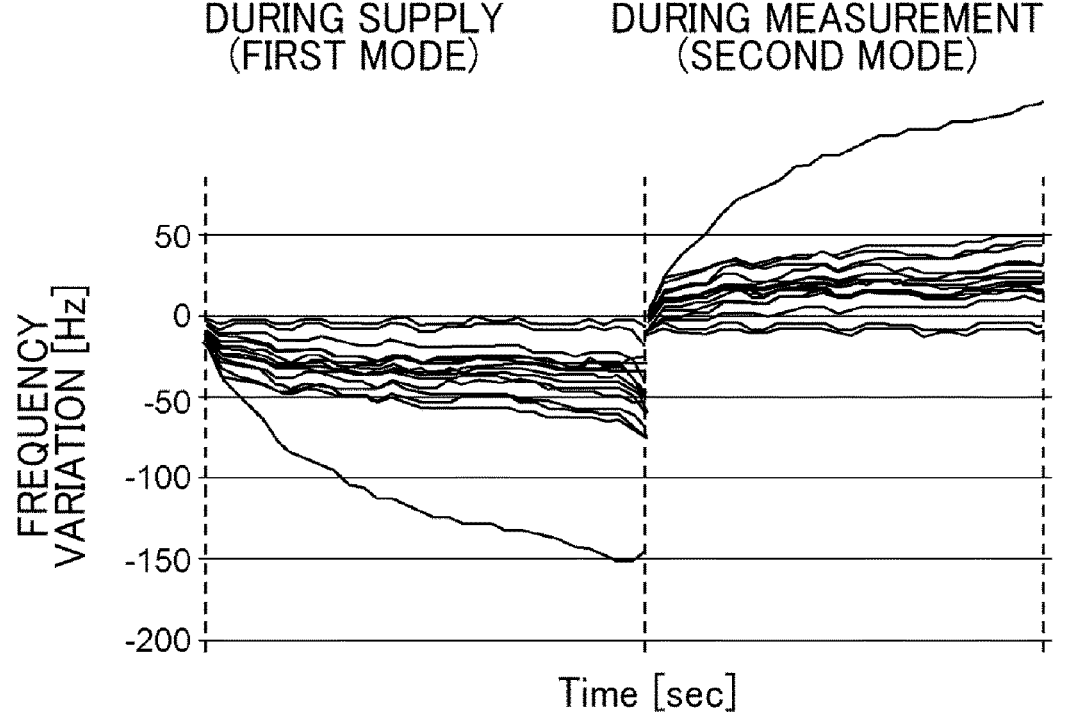
FIG. 4B illustrates a temporal variation in an amount of frequency variation based on an output signal from a sensor.
Figure 9A:
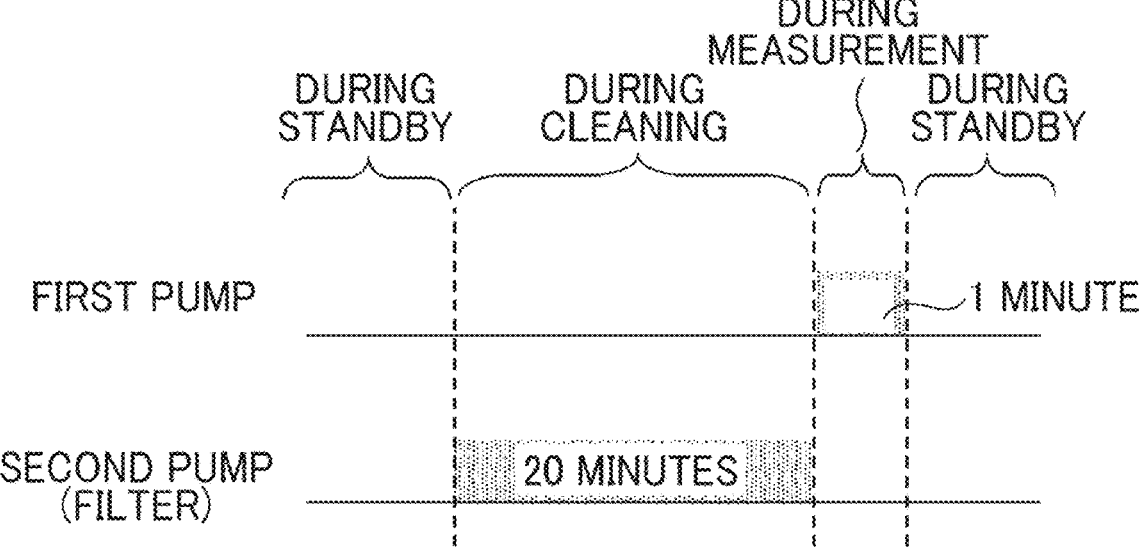
FIG. 9A is a diagram for describing the operation states of pumps in the conventional odor determination method.
Figure 9B:
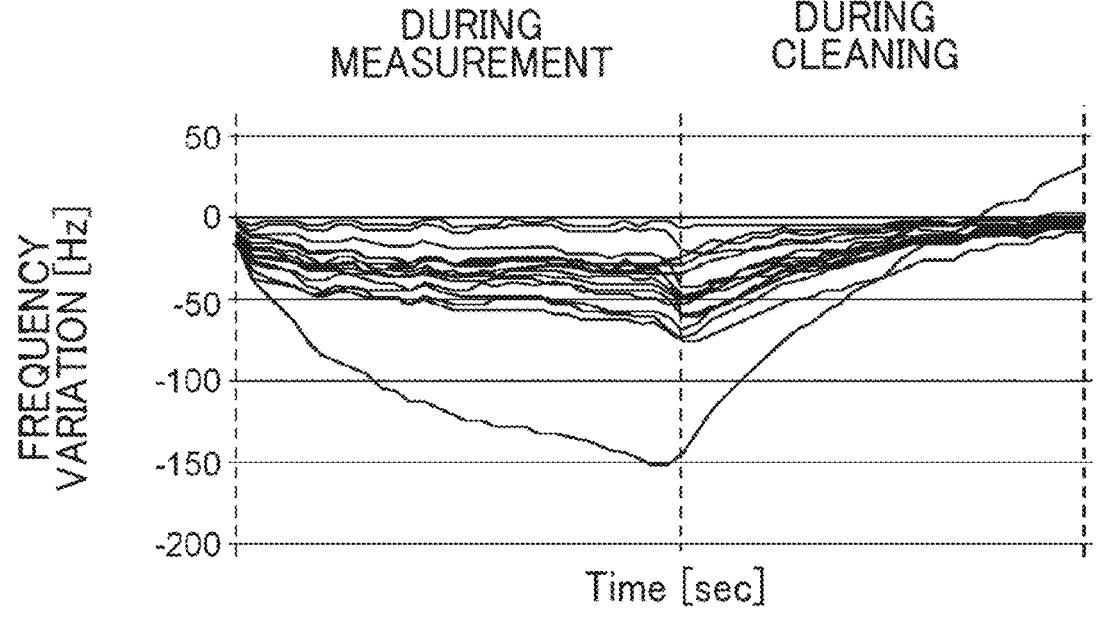
FIG. 9B illustrates a temporal variation in an amount of frequency variation based on an output signal from a sensor.

FIGS. 4A and 4B correspond to FIGS. 9A and 9B, respectively. FIG. 4A illustrates an example of the time spent in each step in the odor determination method of the present embodiment. FIG. 4B illustrates a temporal variation in an amount of frequency variation in each step in the odor determination method, which is calculated based on the measurement result of each odor sensor 90 of the odor determination system 1 illustrated in FIG. 1. FIG. 9A illustrates an example of the time spent in each step in the conventional odor determination method. FIG. 9B illustrates a temporal variation in an amount of frequency variation in each step in the odor determination method, which is calculated based on the measurement result in each odor sensor of the odor determination system.

Conventional Odor Determination Method

A conventional odor determination method will be described with reference to FIG. 7A, FIG. 7B, FIG. 8, FIG. 9A, and FIG. 9B.

As illustrated in FIG. 7A, an odor measurement device 102 used in the conventional odor determination method has the same basic configuration as the odor measurement device 2 of the present embodiment, and includes the housing chamber 20, the odor sensors 90, the filter 7, the first pump 4A (not illustrated), and the second pump 4B (not illustrated).

In the odor measurement device 102, odor determination is performed based on a variation in the resonant frequency of the quartz oscillator of the odor sensor when an odorous substance is adsorbed on the adsorption film 92.

In accordance with the flowchart of FIG. 8 and with reference to FIG. 7A, FIG. 7B, FIG. 9A, and FIG. 9B, the conventional odor determination method will be described.

When the odor determination process is started, the second pump 4B is operated to clean the odor sensor 90 (S11, cleaning step).

When the second pump 4B is operated, outside air 150 passes through the filter 7 and becomes a cleaning gas 151 to be supplied into the housing chamber 20. The outside air 150 is a gas containing an odor to be determined. In S11, the gas 151 that has passed through the filter 7 is supplied into the housing chamber 20. The gas 151 that has passed through the filter 7 is a gas from which odorous substances and moisture have been removed. By supplying the gas 151, the adsorption film 92 of the odor sensor 90 is cleaned. As a result, the odorous substance adsorbed on the adsorption film 92 is desorbed and cleaned, and the adsorption film 92 is brought into an initial state in which no odorous substance is adsorbed.

This cleaning step takes, for example, 20 minutes. Although an example in which the gas 151 obtained through the filter 7 is used as the gas used in the cleaning step has been described here, an inert gas or ozone may be used as the cleaning gas.

Then, the second pump 4B is stopped, the first pump 4A is operated, and the odorous substance is measured by the odor sensor 90 (S12, measurement step).

When the first pump 4A is operated, the gas (outside air) 150 containing the odor to be determined is supplied into the housing chamber 20. The adsorption film 92 of the odor sensor 90 is exposed to the gas 150 containing the odor to be determined. Thus, the odorous substance is adsorbed onto the adsorption film 92 of the odor sensor 90. A variation in resonant frequency due to the adsorption is measured by the odor sensor 90. The determination of the odorous substance is performed based on the measurement result. The measurement step takes, for example, one minute.

The process waits until the next measurement (S13), and it is determined whether remeasurement is to be performed (S14). Whether remeasurement is to be performed is determined by the control unit 14 based on, for example, information on the instruction input by the user using the data terminal 3. When it is determined that remeasurement is to be performed (YES), the process returns to S11 and the process is repeated. When it is determined that remeasurement is not to be performed (NO), a series of processes related to the odor determination is ended.

As illustrated in FIG. 9A, although the processing time spent in each step depends on the volume of the housing chamber 20 and the like, as an example, the cleaning step S11 takes 20 minutes, and the measuring step S12 takes 1 minute.

In the conventional single odor determination process, the total operation time of the first and second pumps is 21 minutes, and the operation time of the filter 7 is 20 minutes.

As described above, in the conventional odor determination method, since the odor is determined based on the variation in resonant frequency caused by the adsorption of the odorous substance on the adsorption film 92 of the odor sensor 9, it is necessary to sufficiently clean the adsorption film 92 for accurate measurement, and it takes a long time for the cleaning. The time required for sufficient cleaning varies depending on the concentration of the odorous substance, and it is difficult to determine how much time is required for the cleaning step to achieve sufficient cleaning. For this reason, it is ideal that the adsorption film is brought into an initial state in which the odorous substance or the like is not adsorbed by the cleaning step of S11 performed before the measurement step, but it is difficult to perform the cleaning efficiently in terms of time.

When sufficient cleaning is not performed and the odorous substance remains on the adsorption film 92 at the start of the next measurement step, for example, as illustrated in FIG. 7B, a difference b occurs between the value of the resonant frequency detected at the time M2 of the start of the next measurement step and the value of the resonant frequency detected at the time M1 of the start of the previous measurement step. It is assumed that the adsorption film 92 at the time M1 of the start of the previous measurement step is in an initial state in which no odorous substance is adsorbed. In the next measurement step, the variation in resonant frequency is measured in a state in which the reference point at the start of the measurement step has a difference b from the previous reference point. As illustrated in the figure, in the adsorption step, which is the measurement step, the resonant frequency rapidly varies in a short time from the start of adsorption. For this reason, when the next measurement step is performed in a state in which the odorous substance remains on the adsorption film 92, that is, in a state in which the reference point at the start of measurement is shifted, accurate measurement cannot be performed, and it is difficult for the conventional odor determination method to perform stable and accurate measurement. Further, for example, when the measurement is continuously performed by repeating the cleaning step and the measurement step, it is difficult to set the time spent for the cleaning step as described above. Therefore, it is difficult to stably make the state of the adsorption film 92 the same at the start of each measurement step, and the conventional odor determination method is not so suitable for continuous measurement.

Furthermore, in the conventional odor determination method, the adsorption film may not be sufficiently cleaned in the cleaning step, and moisture may remain in the adsorption film in addition to the remaining odorous substance that has not been desorbed. When moisture remains, the moisture remaining in the adsorption film greatly affects the output signal in the measurement step. Therefore, even when odor determination is performed based on the variation in the output signal of each odor sensor, it is difficult to perform accurate determination.

It may be considered that information on variation in resonant frequency caused by humidity is acquired in advance, and the variation caused by humidity is subtracted from an actual measurement value based on the information. However, if there is moisture that has been adsorbed in the previous measurement step and remains, because of the influence of the moisture, even when the variation caused by the humidity of the gas containing the odorous substance is subtracted from the actual measurement value, the variation caused by the moisture remaining in the adsorption film cannot be subtracted, and it is difficult to accurately calculate the variation caused by the odorous substance and to accurately detect the strength of the odor.

As described above, in the conventional odor determination method, it is difficult to stably equalize the adsorption state of the adsorption film 92 between the time M1 of the start of the previous measurement step and the time M2 of the start of the next measurement step, and thus it is difficult to perform accurate measurement.

Odor Determination Method of Present Embodiment

The odor determination method of the present embodiment will be described with reference to FIG. 2A, FIG. 2B, FIG. 3, FIG. 4A, and FIG. 4B.

In the odor determination method by the odor measurement device 2 of the present embodiment, the second gas is supplied to the adsorption film 92 on which the odorous substance is adsorbed, and the odor determination is performed based on a variation in resonant frequency of the quartz oscillator of the odor sensor when the odorous substance is desorbed from the adsorption film 92.

The odor determination method of the present embodiment will be described with reference to FIG. 2A, FIG. 2B, FIG. 4A, and FIG. 4B in accordance with the flowchart of FIG. 3.

When the odor determination process is started, the first pump 4A is operated, and a process of supplying the first gas 50 to the odor sensor 90 is performed (S1, supply step). The first gas 50 is the outside air in the environment to be determined, and is a gas containing the odor to be determined.

When the first pump 4A is operated, the first gas 50 containing the odor to be determined is supplied into the housing chamber 20, and the adsorption film 92 of the odor sensor 90 is exposed to the first gas 50. Thus, the odorous substance is adsorbed onto the adsorption film 92 of the odor sensor 90. The supply step takes, for example, 20 minutes.

Then, the first pump 4A is stopped, the second pump 4B is operated, and measurement is performed (S2, measurement step).

The operation of the second pump 4B causes the first gas 50 to pass through the filter 7 and become the second gas 51 to be supplied into the housing chamber 20. When the second gas 51 is supplied to the odor sensor 90, the odorous substance adsorbed on the adsorption film 92 of the odor sensor 90 is desorbed. A variation in resonant frequency associated with this desorption is measured. The amount of the odorous substance is determined based on the measurement result. The measurement step takes, for example, one minute.

The measurement step will be described in more detail.

In the measurement step, the information on the resonant frequency in the desorption process detected by each odor sensor 90 is output to the determination unit 15 by the control unit 14. In addition, the information on the humidity of the first gas 50 detected by the humidity sensor 93 is output to the determination unit 15 by the control unit 14.

Under the control by the control unit 14, the determination unit 15 acquires, from the database 34 of the data terminal 3, information related to desorption and information related to humidity corresponding to the information on the humidity detected by the humidity sensor 93. The determination unit 15 refers to the information related to desorption acquired from the database 34, and determines the amount of the odorous substance using the information on the resonant frequency detected by each odor sensor 90. Further, the determination unit 15 determines the odor to be determined on the basis of the radar charts illustrated FIG. 6A and FIG. 6B created based on the measurement result of each odor sensor 90. The strength of the odor is determined based on the size (area) of the radar chart.

The result of the determination made by the determination unit 15, the detection result of each odor sensor 90, and the like are transmitted to the data terminal 3, and the user can check these results on the display unit 32.

The process waits until the next measurement (S3), and it is determined whether remeasurement is to be performed (S4). Whether remeasurement is performed is determined by the control unit 14 based on, for example, information on the instruction input by the user using the data terminal 3. When it is determined that remeasurement is to be performed (YES), the process returns to S11 and the process is repeated. When it is determined that remeasurement is not to be performed (NO), a series of processes related to the odor determination is ended.

As illustrated in FIG. 4A, although the processing time of each step depends on the internal volume of the housing chamber 20 and the like, as an example, the supply step S1 takes 20 minutes and the measurement step S2 takes 1 minute. The time spent for each step is not limited to the above.

In the single odor determination method of the present embodiment, the total operation time of the first and second pumps is 21 minutes, and the operation time of the filter 7 is 1 minute.

As described above, in the odor determination method according to the present embodiment, it is possible to significantly reduce the operation time of the filter 7. Therefore, the frequency of filter replacement can be reduced, and the operating efficiency can be improved as compared with the conventional method.

For comparison, the volume of the housing chamber 20 used in the conventional measurement method is the same as that of the housing chamber 20 in the present embodiment, the gas used is the same, and the processing conditions are the same.

As illustrated in FIG. 2B, in the supply step, the resonant frequency rapidly varies in a short time from the start of supply, then varies slowly, and then saturates and becomes constant. In other words, since the resonance frequency is substantially constant in the latter half of the supply step, even when the next measurement is performed in a state where the first gas cannot be sufficiently applied to the adsorption film 92, it is possible to sufficiently reduce the difference a between the reference point at the time M1 of start of the previous measurement and the reference point at the time M2 of start of the next measurement step. That is, the adsorption state in the adsorption film 92 at the time M1 of the start of the previous measurement and the reference point at the time M2 of the start of the next measurement step can always be adjusted to be a state in which the adsorption film 92 is substantially saturated with the odorous substance, and stable and accurate measurement can be performed.

Further, in the present embodiment, since the adsorption film 92 at the start of the measurement is substantially saturated with the odorous substance, even when the odorous substance remains on the adsorption film 92 at the end of the measurement step, the next measurement step is not affected, and it is not necessary to sufficiently clean the adsorption film 92 for the next measurement step unlike the related art. Thus, the operation time of the filter can be shortened and the frequency of filter replacement can be reduced as compared with the related art.

In addition, for example, in the case in which the measurement is performed by continuously repeating the supply step and the measurement step, the adsorption state of the adsorption film 92 at the start of each measurement step can be always made to be a state in which the adsorption film 92 is substantially saturated with the odorous substant.

Here, in the conventional odor determination method described above, the measurement step is a step of causing the adsorption film to adsorb the odorous substance, and the measurement time is, for example, one minute. In a case in which the cleaning step and the measurement step are continuously repeated in the conventional odor determination method, since the adsorption time in the measurement step is short, for example, if the concentration distribution of the odorous substance is uneven in the outside air to be measured, the amount of adsorption of the odorous substance varies in each measurement, and the measured value is likely to vary. As described above, in the conventional odor determination method, measurement values may vary in each measurement, reproducibility is low, and it is difficult to measure an odorous substance with high accuracy. In addition, although it is possible to make the time spent in the measurement step longer so as not to cause variations in the measured values, the time spent in the cleaning step is also long. Therefore, the time required for one measurement process of the odorous substance is long, resulting in lower operating efficiency.

In contrast, in the present embodiment, the supply step is a step of causing the adsorption film to adsorb the odorous substance, and the supply time is, for example, 20 minutes. The time spent for the adsorption step corresponding to the supply step of the present embodiment is sufficiently longer than the time spent for the adsorption step corresponding to the measurement step in the conventional odor determination method. Accordingly, for example, even when the concentration distribution of the odor is uneven in the outside air to be measured, it is possible to reduce the influence of the unevenness in the concentration distribution of the odor. Since the state of the adsorption film at the start of each measurement is always set to a state in which the adsorption film is substantially saturated with the odorous substance and each measurement is performed based on this state, it is possible to stably and continuously perform highly accurate measurement with high reproducibility. In addition, as illustrated in FIG. 2B, in the measurement step corresponding to the desorption step, the resonant frequency rapidly varies in a short time from the start of measurement, and thus it is possible to set the time spent for the measurement step to be short. Therefore, the time required for one odor determination process can be shortened, and highly accurate determination can be performed while improving the operating efficiency.

As described above, the odor determination method of the present embodiment is also suitable for continuous measurement. In FIG. 2B, it is assumed that the adsorption film 92 at the time M1 of the start of the previous measurement step is in a state in which the adsorption film 92 is saturated with the odorous substance.

Further, in the odor determination method of the present embodiment, the adsorption film 92 at the start of measurement adsorbs moisture in the outside air in addition to the odorous substance in the outside air, which is the first gas containing the odor to be determined. That is, in each measurement, the adsorption film at the start of measurement is always in a state in which the information on the odor and humidity of the outside air is reflected almost as it is. Therefore, the odor determination method of the present embodiment is not affected by the moisture that has not been removed in the cleaning step and remains in the adsorption film unlike the conventional odor determination method, and can easily determine the type of the odor by taking out the information related to desorption corresponding to the information on the humidity of the first gas measured and acquired by the humidity sensor 93 from the database 34 and referring to the information related to desorption. Furthermore, the amount of the odorous substance can be calculated more accurately by using the information on the humidity stored in the database 34.

As described above, the odor determination method of the present embodiment can perform humidity correction with higher accuracy than the conventional odor determination method.

Odor Determination Based on Variation in Resonant Frequency at Time of Desorption It was confirmed from the results illustrated in FIG. 5 and FIG. 6A to FIG. 6D that the odor determination can be performed based on the variation in frequency at the time of desorption of the odorous substance from the adsorption film in the same manner as the odor determination based on the variation in frequency at the time of adsorption of the odorous substance onto the adsorption film. In FIG. 5 and FIG. 6A to FIG. 6D, "EXAMPLE" refers to an example using the odor determination method of the present embodiment, and "COMPARATIVE EXAMPLE" refers to an example using the conventional odor determination method.

Figure 5:
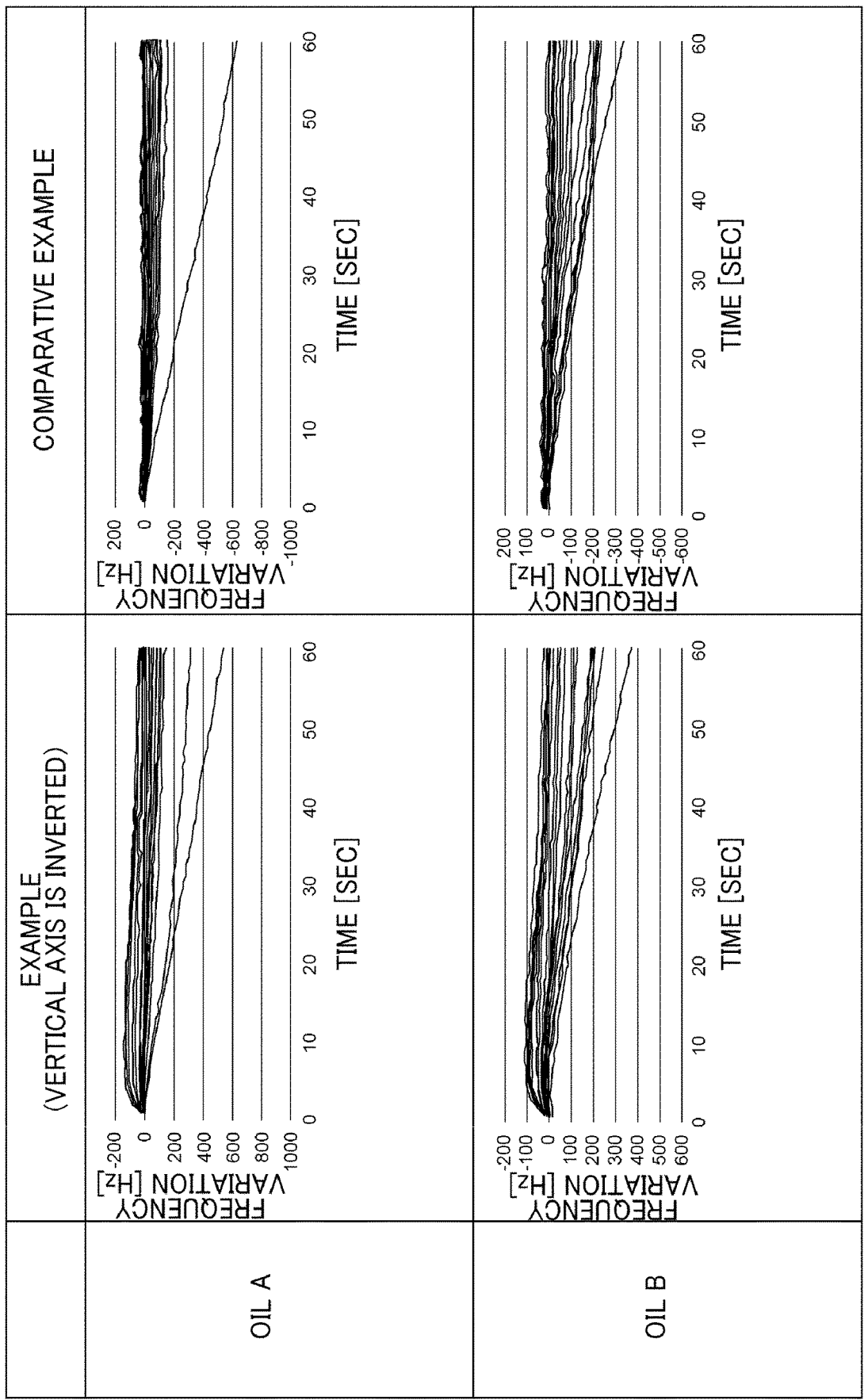
FIG. 5 is a diagram for comparing measurement results when two types of oils different from each other are measured using the odor determination method of the embodiment and a conventional odor determination method.

FIG. 5 presents measurement results obtained by the odor determination method of the present embodiment and the conventional odor determination method using two types of oil A and oil B. The oil A and the oil B differ in the quantitative proportion of odorous substances. At the time of odor determination, a gas emitted from the oil A and a gas emitted from the oil B are used as gases containing odorous substances to be determined. FIG. 5 illustrates the temporal variation in the frequency variation calculated based on the measurement result of each of the 16 odor sensors 90. In FIG. 5, in the graph of the example, the vertical axis is inverted.

FIG. 6A and FIG. 6B are radar charts illustrating the proportional relationship among the amounts of variations in resonant frequencies detected by the respective odor sensors 90 when the gases emitted from the mutually different oils A and B are measured using the odor determination method of the present embodiment.

FIG. 6C and FIG. 6D are radar charts illustrating the proportional relationship among the amounts of variations in resonant frequencies detected by the respective odor sensors 90 when the gases emitted from the mutually different oils A and B are measured using the conventional odor determination method. In FIG. 6C and FIG. 6D, the radar chart is created based on the maximum value of the amount of variation in resonant frequency calculated based on the resonant frequency detected by each odor sensor 90.

In FIG. 6A to FIG. 6D, the results of 3 measurements are presented in the comparative example, and the results of 20 measurements are presented in the example.

As presented in FIG. 5, it is confirmed that the sensors that respond to both the oil A and the oil B are the same odor sensors between the example and the comparative example, and the odor determination can be performed based on the variation in frequency at the time of desorption of the odorous substance from the adsorption film in the same manner as the odor determination based on the variation in frequency at the time of adsorption of the odorous substance onto the adsorption film.

In addition, as presented in FIG. 6A to FIG. 6D, also in the radar charts, it is confirmed that the sensors that respond to both the oil A and the oil B are the same odor sensors between the example and the comparative example, and the odor determination can be performed based on the variation in frequency at the time of desorption of the odorous substance from the adsorption film in the same manner as the odor determination based on the variation in frequency at the time of adsorption of the odorous substance onto the adsorption film. Further, as presented in FIG. 6A and FIG. 6B, radar charts having substantially the same shape can be obtained even in a plurality of measurements, and it is confirmed that the odor determination based on the variation in frequency at the time of desorption of the odorous substance from the adsorption film has high reproducibility. In addition, it is confirmed that the example tends to have less variation than the comparative example and has higher reproducibility than the conventional odor determination method.

As described above, in the present embodiment, the operating efficiency is improved, and the odor determination can be performed with high accuracy.

Although the embodiment of the present invention has been described above, it is needless to say that the present invention is not limited to the above-described embodiment and various modifications can be made.

In the above-described embodiment, the QCM is used as an example of the odor sensor, but this does not intend to suggest any limitation. Any sensor may be used as long as it has an adsorption film capable of adsorbing and desorbing an odorous substance and outputs a signal corresponding to the adsorption of the odorous substance. For example, although the quartz oscillator has been described as an example of the oscillation element used in the odor sensor, other oscillation elements such as a ceramic oscillator, a surface acoustic wave element, a cantilever, and a diaphragm that can determine a physical change such as an increase in weight or an increase in expansion stress due to adsorption of an odorous substance on an adsorption film and convert the physical change into an electric signal can also be applied. In addition, as the odor sensor, a semiconductor type sensor using a resistance value change due to adsorption of an odorous substance of the semiconductor as an adsorption film, that is, an output signal change may be used.

In addition, in the above-described embodiment, an example in which a plurality of odor sensors are provided is described, but one odor sensor may be provided. In this case, the present embodiment is applicable to the measurement of the amount or concentration of a known odorous substance. Also in this case, the operating efficiency is improved and the odor determination can be performed with high accuracy.

In the above-described embodiment, the control unit 14 and the determination unit 15 are provided in the odor measurement device 2 on which the odor sensors 90 are installed, but this does not intend to suggest any limitation. For example, at least one of the control unit 14 or the determination unit 15 may be provided in an external device other than the odor measurement device 2, for example, the data terminal 3 or a cloud server. In the above-described embodiment, the database 34 is provided in the data terminal 3. However, the database 34 may be provided in the odor measurement device 2 or a cloud server, and the entire odor determination system 1 may include a sensor, a control unit, a determination unit, and a database.

In the above embodiment, the first gas is supplied to the housing chamber 20 by the first pump 4A, and the second gas is supplied to the housing chamber 20 by the second pump 4B. However, the first gas and the second gas may be supplied to the housing chamber 20 by one pump. In this case, for example, a supply path for the first gas, a supply path for the second gas, and a path switching valve for switching between the two supply paths are provided, and a filter for removing an odorous substance and moisture is provided in the supply path for the second gas.

The humidity sensor 93 may be installed not only inside the housing chamber 20 but also outside the housing chamber 20, and humidity correction may be performed based on the measurement data of each odor sensor based on the output of each of the humidity sensors installed inside and outside the housing chamber 20.

In addition, in the above-described embodiment, an example in which a plurality of odor sensors are provided is described, but one odor sensor may be provided. For example, when the gas to be determined is known, the strength of the odor can be determined from the information on the output signal 1 in the desorption process using the odor sensor.

What is claimed is:

1. An odor measurement device comprising:
a sensor having an adsorption film that adsorbs an odorous substance and outputting a signal corresponding to adsorption of the odorous substance on the adsorption film;
a housing chamber that houses the sensor;
a first pump configured to supply a first gas containing an odorous substance to the housing chamber;
a second pump configured to supply a second gas for desorbing the odorous substance from the adsorption film to the housing chamber; and
a control device including:
a determination unit configured to measure the odorous substance on the basis of information on an output signal of the sensor in a desorption process in which the odorous substance is desorbed from the adsorption film, and a control unit capable of sequentially executing a first mode in which the first gas is supplied to the housing chamber and a second mode in which the second gas is supplied to the housing chamber and the odorous substance is measured by the determination unit.

2. The odor measurement device according to claim 1, wherein the control unit executes the first mode for a period longer than that in the second mode.

3. The odor measurement device according to claim 1, wherein the determination unit measures the odorous substance on the basis of the information on the output signal of the sensor in the desorption process in which the odorous substance adsorbed on the adsorption film in the first mode is desorbed from the adsorption film in the second mode.

4. The odor measurement device according to claim 1, wherein the determination unit measures the odorous substance by referring to information on variation in an output signal in the desorption process for a plurality of different odorous substances measured in advance by the sensor.

5. The odor measurement device according to claim 4,
wherein the information on variation in the output signal in the desorption process is measured in advance for a plurality of different humidity conditions, and
wherein the determination unit measures the odorous substance by using information on humidity of the first gas acquired by a humidity sensor and referring to the information on variation in the output signal in the desorption process.

6. The odor measurement device according to claim 1, further comprising:
a filter that adsorbs an odorous substance contained in the first gas,
wherein the second pump supplies a gas that has passed through the filter to the housing chamber as the second gas.

7. The odor measurement device according to claim 6, wherein the filter includes at least one of activated carbon, silica gel, zeolite, or allophane.

8. The odor measurement device according to claim 1, wherein the sensor is provided in a plurality, and the plurality of odor sensors have different detection sensitivities depending on respective odorous substances.

* * * * *